United States Patent
Gartstein et al.

(10) Patent No.: US 8,973,851 B2
(45) Date of Patent: Mar. 10, 2015

(54) APPARATUS AND METHODS FOR PRODUCING CHARGED FLUID DROPLETS

(75) Inventors: Vladimir Gartstein, Mason, OH (US); James C Horney, Cincinnati, OH (US); Alan David Willey, Cincinnati, OH (US); Claire Rebecca Yates, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1102 days.

(21) Appl. No.: 12/818,494

(22) Filed: Jun. 18, 2010

(65) Prior Publication Data

US 2011/0000975 A1    Jan. 6, 2011

Related U.S. Application Data

(60) Provisional application No. 61/222,239, filed on Jul. 1, 2009, provisional application No. 61/222,271, filed on Jul. 1, 2009, provisional application No. 61/222,282, filed on Jul. 1, 2009.

(51) Int. Cl.
*B05B 5/00* (2006.01)
*B03C 3/16* (2006.01)

(52) U.S. Cl.
CPC ........................ *B03C 3/16* (2013.01)
USPC ........ 239/690; 239/145; 239/690.1; 239/696; 128/200.14

(58) Field of Classification Search
USPC .......................... 239/3, 145, 690, 690.1, 696; 128/200.14
See application file for complete search history.

(56) References Cited

U.S. PATENT DOCUMENTS

| | | | |
|---|---|---|---|
| 3,929,135 A | 12/1975 | Thompson | |
| 4,748,043 A * | 5/1988 | Seaver et al. | 239/696 |
| 5,382,410 A * | 1/1995 | Peltier | 239/34 |
| 6,251,322 B1 | 6/2001 | Phillips et al. | |
| 6,457,470 B1 * | 10/2002 | Coffee | 239/690 |
| 6,471,753 B1 | 10/2002 | Ahn et al. | |
| 6,607,579 B2 | 8/2003 | Willey et al. | |
| 6,607,586 B2 | 8/2003 | Willey et al. | |
| 6,656,253 B2 | 12/2003 | Willey et al. | |
| 6,684,879 B1 * | 2/2004 | Coffee et al. | 128/200.14 |
| 7,160,391 B2 | 1/2007 | Willey et al. | |
| 7,261,915 B2 | 8/2007 | Boulais et al. | |
| 7,360,724 B2 | 4/2008 | Willey et al. | |
| 7,390,384 B2 | 6/2008 | Fang et al. | |
| 7,410,683 B2 | 8/2008 | Curro et al. | |
| 7,410,983 B2 | 8/2008 | Watts et al. | |

(Continued)

FOREIGN PATENT DOCUMENTS

| | | |
|---|---|---|
| RU | 2063218 | 7/1996 |
| RU | 2342999 | 1/2009 |
| SU | 1007746 | 3/1983 |

OTHER PUBLICATIONS

International Search Report dated Sep. 20, 2010 containing 8 pages.

*Primary Examiner* — Steven J Ganey
(74) *Attorney, Agent, or Firm* — Jeffrey V Bamber; Brent M Peebles

(57) ABSTRACT

Disclosed herein is the apparatus that produces very small or nano-sized, charged droplets and the methods for producing such charged fluid droplets. This apparatus avoids the problems known to exist with using spray nozzles having very small orifices to produce such small fluid droplets, those problems including clogging of the nozzles.

31 Claims, 10 Drawing Sheets

(56) References Cited

U.S. PATENT DOCUMENTS

| | | |
|---|---|---|
| 2002/0185004 A1 | 12/2002 | Willey et al. |
| 2003/0079608 A1 | 5/2003 | Willey et al. |
| 2003/0196552 A1 | 10/2003 | Willey et al. |
| 2004/0089156 A1 | 5/2004 | Gartstein et al. |
| 2005/0124512 A1 | 6/2005 | Woo et al. |
| 2006/0081178 A1 | 4/2006 | Willey et al. |
| 2006/0081728 A1 | 4/2006 | Willey et al. |
| 2006/0214020 A1* | 9/2006 | Suda et al. .................. 239/690 |
| 2007/0033920 A1 | 2/2007 | Song |
| 2008/0225087 A1 | 9/2008 | Lee et al. |
| 2008/0249490 A1 | 10/2008 | Carlucci et al. |
| 2009/0289343 A1 | 11/2009 | Chiu et al. |

* cited by examiner

APPARATUS AND METHODS FOR PRODUCING CHARGED FLUID DROPLETS

CROSS REFERENCE TO RELATED APPLICATION

This application claims the benefit of U.S. Provisional Application No. 61/222,239 filed Jul. 1, 2009; and U.S. Provisional Application No. 61/222,271 filed Jul. 1, 2009; and U.S. Provisional Application No. 61/222,282 file Jul. 1, 2009.

FIELD OF THE INVENTION

The presently claimed apparatus produces very small or nano-sized, charged fluid droplets. These droplets may be employed in equipment designed for home and commercial use for among other things, controlling air supply quality.

BACKGROUND OF THE INVENTION

Very small charged fluid droplets have been found useful for a number of uses including applying coating surfaces and capturing dirt in the air. There are a number of advantages to the use of nano droplets for use in a variety of practical applications. For example generating large numbers of nano droplets can be accomplished from low volumes of fluids therein reducing fluid consumption by devices. Nano droplets also have a large surface area to leads to rapid evaporation and efficient delivery of an adjuvant, such as perfume into the air. Nano droplets are easily assimilated into an air flow and remain suspended in the air flow whereas larger droplets would deposit onto surfaces of air circulation ducts. These benefits have advantages for a range of applications including but not limited to air cleaning, perfume delivery, delivery of actives to the nasal and oral cavities.

Very small fluid droplets of various sizes may be formed by a number of alternatives. One known alternative for producing these small droplets is an apparatus equipped with a wet emitter where water is pumped through nozzles having very fine orifices to yield very small water droplets. U.S. Pat. No. 6,656,253 discloses air cleaning devices designed with this spray system. The device yields a charged spray of semiconducting water droplets having a first polarity that is introduced to the air flow. Dirt or other particulates in the air are electrostatically attracted to and retained by the spray droplets.

It's been found, however, that such systems experience nozzle failures when for example, minute non-dissolved precipitants and, or foreign matter in the fluid clog the nozzles. Even where no solids exist in the fluid, higher fluid viscosity can sufficiently interfere with the fluid flow through the nozzles and fail to create the desired sized droplets. Delivering consistent fluid pressure across a plurality of nozzles when issues such as those above or other exist is a technical challenge faced by those skilled in the art.

Alternative approaches for eliminate nozzle related clogging problems encountered when attempting to produce a reliable supply of very small charged particles include using the principle of dry ionization. Dry ionization eliminates the need for a fluid to create charged particles. Devices functioning on the principle of dry ionization are well known in the prior art and typically comprise two electrodes; one at high voltage and the other at some lower electrical potential. This electrical potential drop between the electrodes is applied to produce an electrical field forming a corona or halo around the high voltage electrode. At the point of formation of the corona, the gas in the space between the two electrodes breaks down and releases electrons or ions that travel directly towards the lower potential electrode. In the case of dry ionization air cleaning devices, the break down of the gas, in this case air, leads to the development of ozone that for a number of reasons, too numerous to mention here, is highly undesirable.

SUMMARY OF THE INVENTION

The present invention is an apparatus using a conductive or semi-conductive fluid that moves along a solid or semisolid filament wherein upon applying a high electrical potential to the fluid, the fluid's high electrical potential relative to a second or counter electrode creates a electrical field intensity sufficient to form a stream of small and charged fluid droplets at the filament's apex as the fluid is electrically drawn towards the counter electrode. It's at this point wherein the electrical charge or polarization of the fluid is of sufficient intensity wherein when the fluid is forced into fine fluid jets that are unstable and form a stream of very fine and charged fluid droplets. These fine droplets become charged or polarized upon the separation from fine fluid jets and move towards the counter electrode along the electrostatic field force lines. The counter electrode comprises electrically conductive or semi-conductive or material capable of being polarized (herein after "polarizable") and may or may not serve as a targeted surface for the fluid droplets. This apparatus provides and efficient and reliable method for producing fluid droplets without the commonly known fluid apparatus problems relating to nozzle clogging.

BRIEF DESCRIPTION OF THE DRAWINGS

FIG. 1 A schematic of the fluid charging system;
FIG. 2 A schematic of a fluid feeding system;
FIG. 3 A side view of an air purifying device;
FIG. 4 A schematic of a fluid feeding system;
FIG. 5 A side view of the fluid emitter;
FIG. 5*a* A perspective view of a substrate;
FIG. 6 A cross-sectional view of a substrate;
FIG. 7 An isometric view of a substrate;
FIG. 7*a* A first cross-sectional view of a substrate;
FIG. 7*b* A second cross-sectional view of a substrate;
FIG. 7*c* A third cross-sectional view of a substrate;
FIG. 7*d* A fourth cross-sectional view of a substrate;
FIG. 8 A perspective view of a substrate;
FIG. 9 A schematic view of an eye treatment device;
FIG. 10 A schematic view of an oral treatment device;
FIG. 11 A schematic view of a hard surface treatment device.

DETAILED DESCRIPTION OF THE INVENTION

The present invention provides an apparatus for the production of very small sized charged fluid droplets. These droplets may be positively or negatively charged depending on their ultimate application. This apparatus comprises a fluid supply, a means to electrically charge the fluid and the fluid emitter. The emitter further comprises a substrate having filaments that transport the fluid and facilitate production of fine fluid droplets. Upon fluid communication with substrate, the fluid moves to a point on the filament wherein upon the charging means being in the on position, the fluid is electrically charged. At this point the fluid at the apex of the filament is at its point of greatest or highest electrical field strength. Whereupon a distance between the apex and a point of lowest electrical field strength the fluid spontaneously breaks into very small droplets that are released from the filament, moving towards a point of lower electrical potential including a targeted surfaces. The apparatus of the present invention can be employed in a number of embodiments for specific purposes including surface treatment and air quality controlling technology.

A. Electrically Chargeable Fluids

The electrical chargeable fluid of the present invention can be any fluid or mixture of fluids that is capable of acquiring and maintaining an electrostatic charge and allows the fluid to form a stream of very small droplets. The fluid has physical properties which enable it to be sprayable under given conditions. The ability of fluid to be sprayable by electric field alone is a function of certain physical properties of the fluid which also control droplet size and fluid flow through the substrate and eventually to the apex of the filament. The physical properties of the fluid is primarily those that insure its compatibility with the filaments and where appropriate the substrate. Such physical properties may include, but not limited to viscosity, density, electrical resistivity, surface tension, dielectric constant, flash point, and boiling point or vapor pressure. The fluid's flux measurement (or the flow by demand) between the fluid moving from the layer of the substrate transporting the fluid (hereinafter referred to as the "transport layer") and the apex of the filament must be sufficient to provide form a sustainable stream of very fine and charged fluid droplets at the filament's apex as the fluid is electrically drawn towards the counter electrode, the measurement being at least about 1 nano ml$^3$ of fluid each hour.

Figure 1:
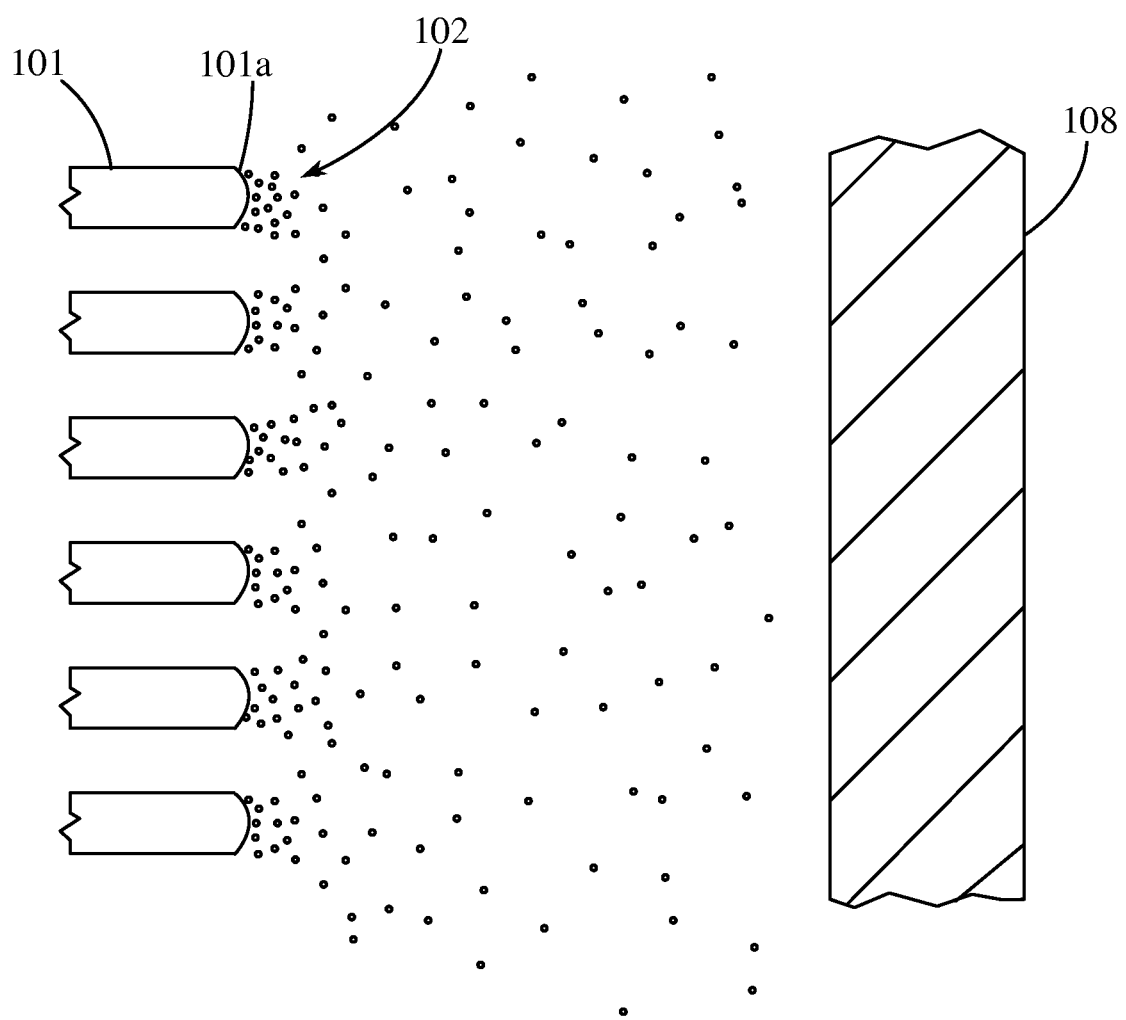

The ability of the fluid to acquire and sustain electrical charge depends on several properties of the fluid. The primary property is the fluids degree of conductivity. If, for example the fluid is insulating thereby having lower conductivity and its resistivity is greater than about 1000 MΩ, then the time required for the fluid to attain a charge will be long and potentially not efficiently function when used with the fluid emitter. On the other hand, where the fluid is too conductive, the fluid's charge will dissipate quickly and not lend itself to breaking into droplets when applied to the fluid emitter. Therefore the electrically chargeable fluid of the present invention should have resistivity between about 1 kΩ/cm to about 1000 MΩ/cm, alternatively from about 100 kΩ/cm to about 500 MΩ/cm as measured by a number of commercial conductivity meters including the WTW® InoLab Cond 7300 bench top conductivity meter available from Cole Parmer, Inc. of Vernon Hills, Ill. The commonly used standard cell has a width of 1 cm, and thus very pure water in equilibrium with air would have a resistance of about $10^6$ ohm/cm, known as a mega ohm, MΩ/cm or 1 S/cm of conductivity A second physical property of the fluid that controls the fluids break up into small droplets is its viscosity. The fluid must possess a viscosity that both allows it to move by capillary action from a fluid's source to the point on the filament where a high field intensity induces the fluid's break up into very small droplets herein referred to as the filament's "apex." FIG. 1 provides an illustration of the chargeable fluid extending to the filament 101 wherein the fluid travels to the filament's apex 101a wherein the presence of the field differential between the charged fluid at the apex and the counter electrode 108 causes the fluid to form the desired small fluid droplets 102. The fluid's viscosity, therefore, must be a consideration in the absence of an electro-mechanical means for delivering the fluid to the filament's apex. Even in the case where such a means for moving the fluid is used, cohesive forces of highly viscous fluids tends to hinder the fluid from breaking into the desired small charged fluid droplets resulting in "stringing" or elongating the fluid into a string as is normally done in the process of making synthetic extruded fibers also referred to as "electro-spinning" and is known in the area of making capillary channel fibers as disclosed in U.S. Pat. No. 6,251,322, Phillips et al. For the purposes of the present invention the fluid viscosity should be less than 1000 centistokes preferably less than 500 centistokes as measured by a Brookfield RVDV-IP viscometer according to the manufacturer's instructions.

Among the physical parameters of the electrically chargeable fluids described above, the fluid used in the present invention must provide benefits that are optimized due to the fluid being in the form of these charged fluid droplets. For example deionised water can be used as the electrically chargeable fluid when it's desired to humidify the air supply or other water loving objects such as tropical plants or keratinous animal or human tissue. Providing it does not hinder the formation of droplets, the fluids can be fortified with other materials that facilitate or heighten the desired benefits.

The electrically chargeable fluid of claim 1 with a viscosity less 1000 centistokes, selected from the group consisting of water-based fluid and oil-based fluids whose selection is based upon it's the fluid's compatibility relative to the material comprising the fluid emitter to transport adequate volumes of the respective fluid to the apex of the filament to form a spray. For example, an oil based fluid will have a molecular attraction to a hydrophobic transport material such as an untreated polypropylene polymer nonwoven or carbon coated porous media for example. These two materials are "compatible." The electrically chargeable fluid therefore is oil-based and selected from fluids that are is immiscible in water and do not dissolve in water.

A water based fluid will wet a hydrophilic material such as cellulose, glass or cotton. This matching of material properties, in regard to the fluid's surface tension and the contact angle of the porous media, is essential to the necessary fluid transport. While water based fluids will wet and move through several hydrophobic structures, as oil will move through many hydrophilic structures, the resulting amount of fluid at the spray tip or filament apex will be inadequate without the proper material-fluid "compatibility." The electrically chargeable fluid therefore is fluid water-based and selected from fluids that are miscible in water and will dissolve in water. Fluids useful in the present invention range from aqueous solutions to those being hydrophobic, non-volatile oils such as those described in U.S. Pat. Nos. 6,607,586; 6,656,253 and 6,607,579. Suitable fluids for the present invention comprise Newtonian and non Newtonian fluids. Water, a polar fluid is a suitable candidate either alone or in the form of aqueous solutions and dispersions an emulsions having materials selected from the group consisting of salts especially isotonic salt solutions, bioactive materials including antimicrobials, bleaches, catalysts, amine and aldehyde reactive species such as those disclosed in U.S. Patent Applications 2005-0124512A1 and 2008-0249490A1. Also these materials include perfuming raw materials, formulated perfumes, surfactants, waxes, oils, polymers, bioavailable, over-the-counter and prescriptive, ingredients including antitussives, decongestants, analgesics, vitamins, and other topical medicinal compounds and agents, coloring materials, color cosmetics, keratinous tissue cleansing, sanitizing, exfoliating, conditioning, styling, toning and moisturizing agents.

Non-aqueous formulations, herein defined solutions having less than 50% water, are also useful as fluids in the invention and may be in various forms including emulsions and dispersions. Such solutions include, but are not limited to sprayable waxes, perfumes, styling polymers, finger nail coatings and the like. Silicone-based, water emulsion are also useful for application of protective coatings and, or high luster or shiny coating on household surfaces, fabrics, car interiors, convertible tops, skin and hair. Also included herein are low basis weight polymer films to provide adhesive release coatings as well as hair styling adhesive polymers. The water to oil ratio of such formulations can impact the voltage required to convert the fluid into droplets, the high voltage activation chemistry reaction rates, airborne particle dispersion pattern characteristics, and droplet size.

B. Fluid Electrical Charging Means

The fluid may be charged by any convenient source of power including direct wiring, or batteries. It will be clear to those skilled in the art that the voltage obtained from these sources must be converted to high voltage suitable for the electrostatic spray process as disclosed in U.S. Pat. Nos. 6,656,253; 6,607,586; 6,607,579 and 7,360,724, each assigned to Procter & Gamble. The charging means can be achieved through commonly available transformers which convert an input voltage to the desired voltage for electrostatic spraying. For example EMCO® High Voltage Corporation, Sutter Creek Calif. provides a wide range of high voltage power sources suitable for the present invention.

Figure 2:
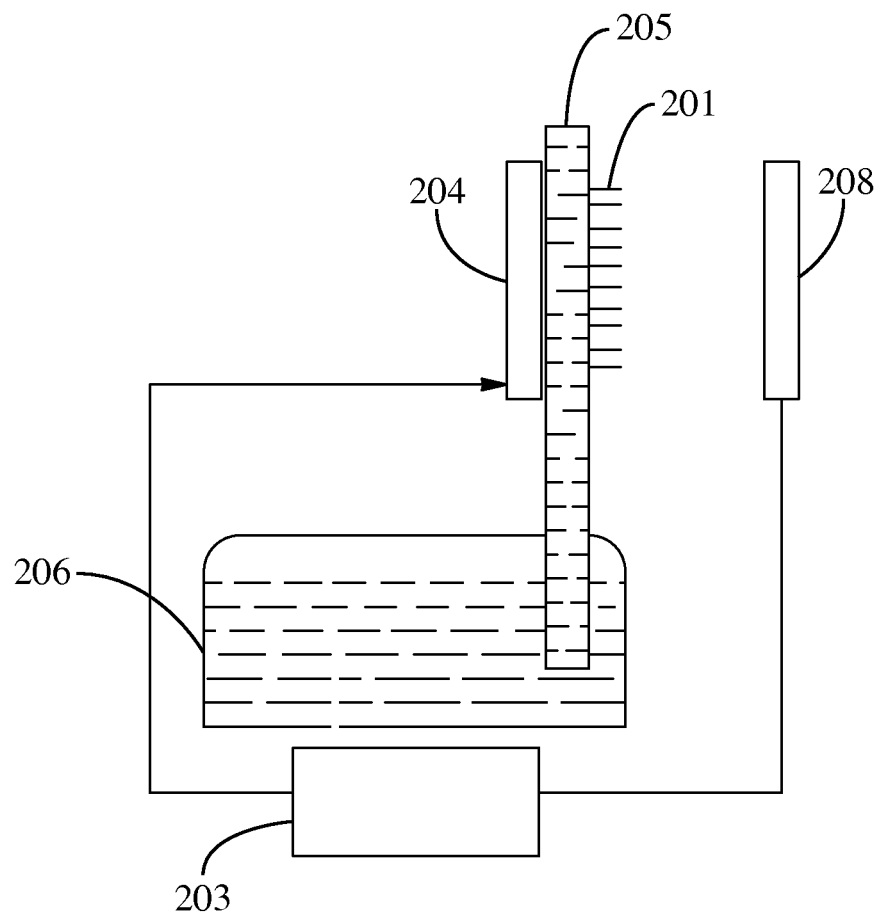
Figure 9:
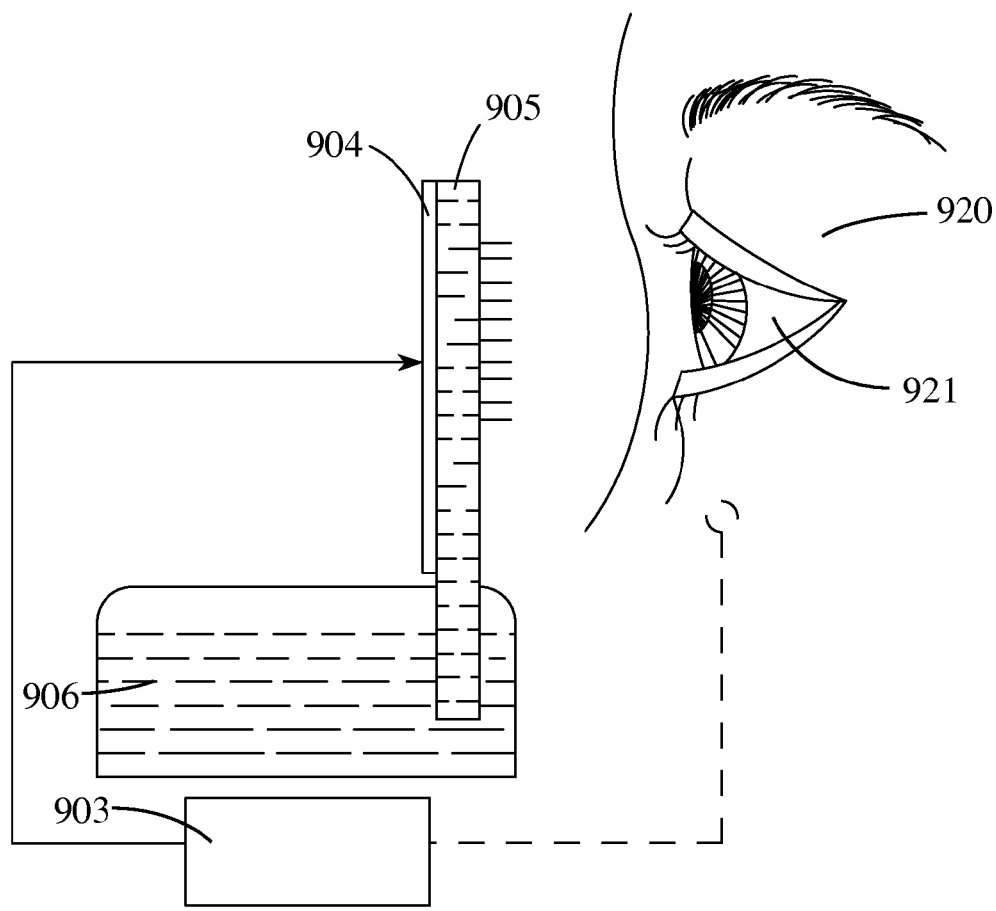
Figure 10:
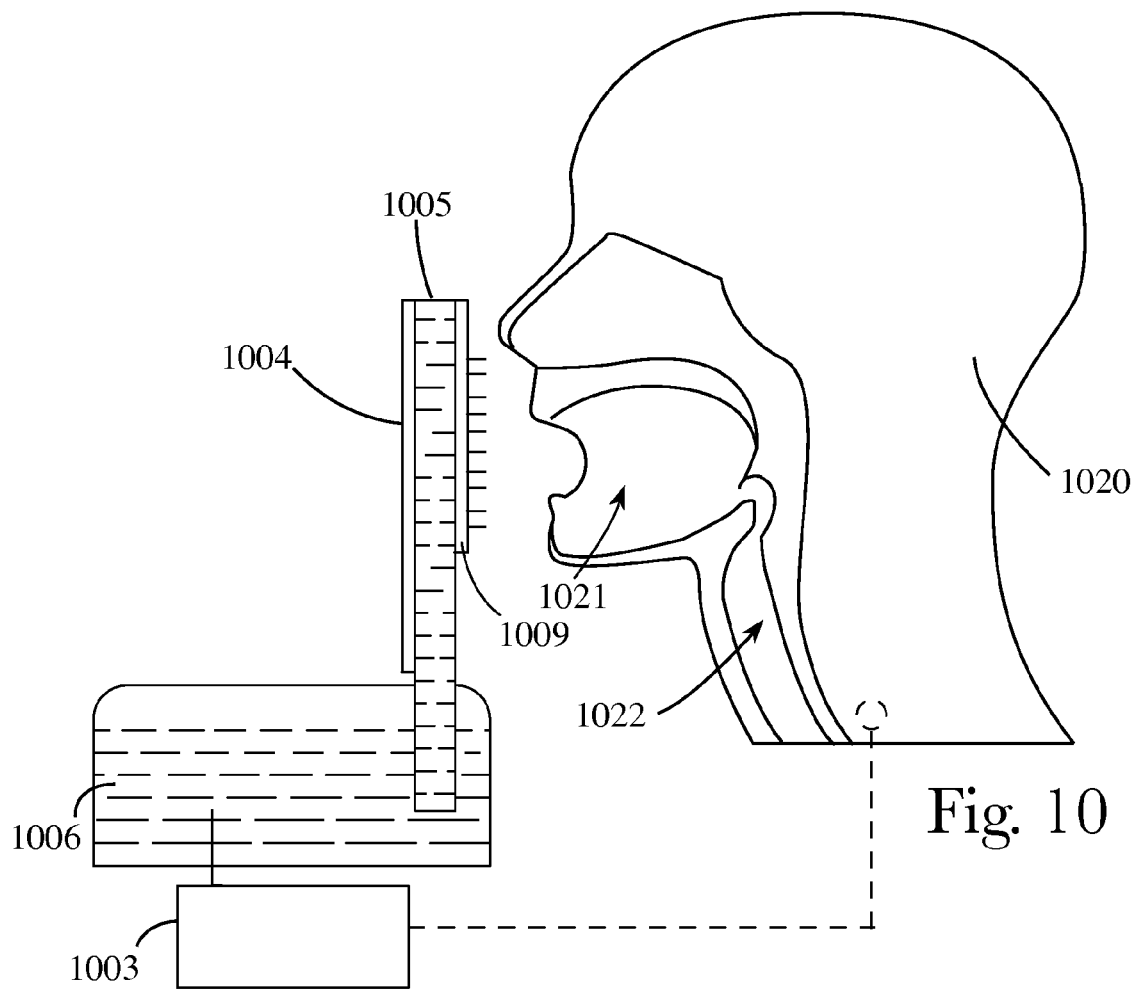
Figure 11:
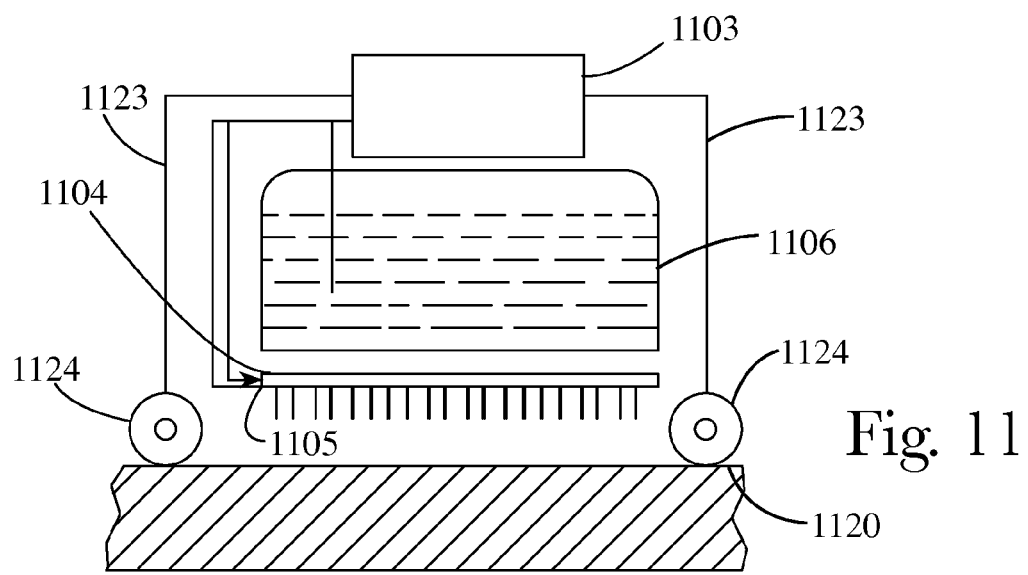

FIG. 2 illustrates one charging system useful in the present invention. The power supply 203 is a direct current source that is connected to a charging electrode in the form of plate 204 in a proximity sufficient to charge fluid saturating the emitter substrate 205 with the fluid formed reservoir 206. In FIG. 2, proximity is defined as direct contact of the adjacent surfaces of the charging electrode 204 and emitter substrate 205. Apparatus Example 1 is a device for purifying air and is illustrated as FIG. 3 wherein the charging electrode 304 is attached to the fluid reservoir 306 and is in direct contact with the fluid. FIG. 9 and FIG. 10 similarly illustrate wherein the charging electrodes are in direct contact with the fluid in the reservoirs. Another alternative is shown in FIG. 11 wherein the charging means is connected to both an electrode in the fluid reservoir 1106 and to the copper plate 1104 directly behind and adjacent to the substrate 1105. Another embodiment is illustrated in FIG. 4 where a fluid is supplied reservoir is in the form of a free-flowing water line 406. The charging electrode 404 is placed within the fluid flow. In this embodiment the charge to the fluid occurs down flow from an insulating restrictor in the water 407 that functions to isolate the electrical charge and thereby avoid conducting electricity back to the source of the fluid such as a water utility.

It will be clear to those skilled in the art that the fluid needs to be in contact with a high voltage electrode. High voltage is generally considered to be greater than 500 volts. The high voltage electrode generally comprise a any suitable material that's compatible with the fluid including, but not limited to metals, graphite, conductive plastic and carbon filled conductive plastic and combination thereof. The electrode's placement may be in very close proximity to the substrate/filaments as in FIG. 2 or more remote from the substrate/filaments as in FIG. 4. Although it generally is not necessary the electrode be closely associated with the substrate/filament, such an alignment reduces loss of electrical power due to the resistive losses from the fluid.

C. Fluid Emitter

Figure 5:
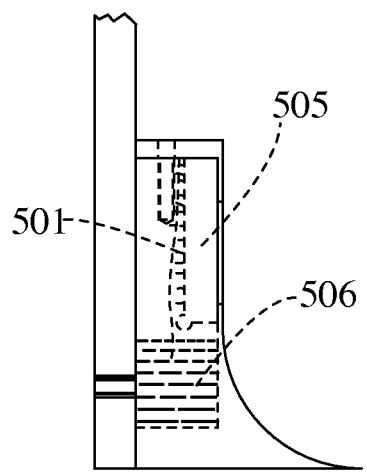
Figure 6:
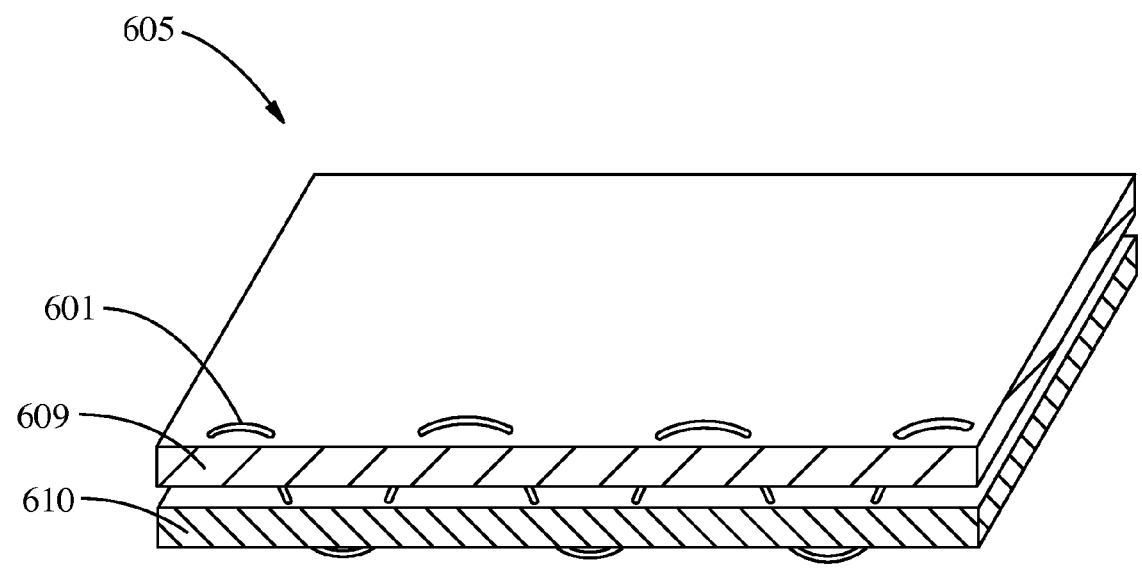

The fluid emitter as illustrated in FIG. 5 comprises a substrate 505 and an evenly spaced, uniform array of wicking filaments 501 affixed thereto. By "affixed" it's meant the filaments and are anchored to the substrate and extend in a direct opposite from the means of attachment. Anchoring the filaments can include any means for attaching including, but not limited to where the filaments are actually formed out of the substrate, or affixed by means including, but not limited to weaving, sonic welding or fusing and gluing. FIG. 6 illustrates an embodiment wherein filaments 601 are woven through substrate 605. The thread 601 may be cut so as to form even length and free-ended filaments on a single side of the substrate 605.

Substrate transport layers and the filaments are chosen based on their ability to transport fluid by capillary action to the filament apex. In FIG. 1, the apex 101a is defined as the point on the filament wherein the charged fluid is at its highest electrical potential relative to an area of lowest electrical potential or ground. When at the apex, the electrically charged fluid forms a stream of very small droplets 102 in the presence of an area of lowest electrical potential 108 or a ground. This process is known in the art as electrostatic spraying or otherwise known as "E-spraying." It's a well understood principle that the filaments apex is rounded or curved in order to most efficiently form the electrical field intensity sufficient to create the charged fluid droplets.

The construction of the substrate must be such that it does not disturb the capillary movement of the fluid to the filaments' apex. Selecting the materials that comprise the substrate's transport layer is generally based on the material's "compatibility" with the chargeable fluid. By "compatibility" it is meant that the material will successfully transport fluid. Furthermore, the substrate must be constructed in such a manner to maintain the fluid's desired characteristics. For example, where the fluid is volatile and subject to accelerated evaporation, the substrate must be constructed so as there is resistance to fluid evaporation while remaining capable of transporting the fluid. This is usually done by constructing the substrate using multiple layers as shown in FIG. 6. The transport layer 610 moves the fluid by the capillary action to their ultimate destination, the filament apex while a second layer 609 or top sheet insulates the fluid. The top sheet while not actually transporting the fluid must not deter its transport and maintain it so it minimizes not only evaporative loss but also its acquired electrical charge.

Figure 5A:
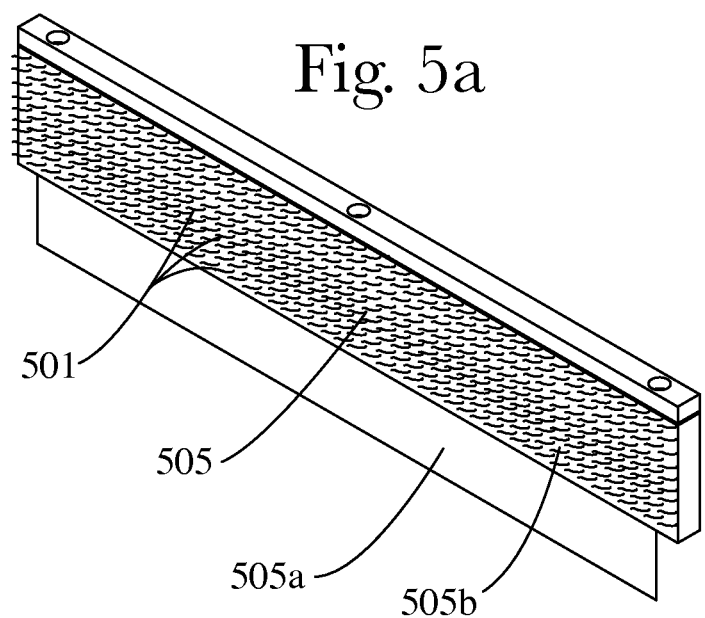
Figure 7:
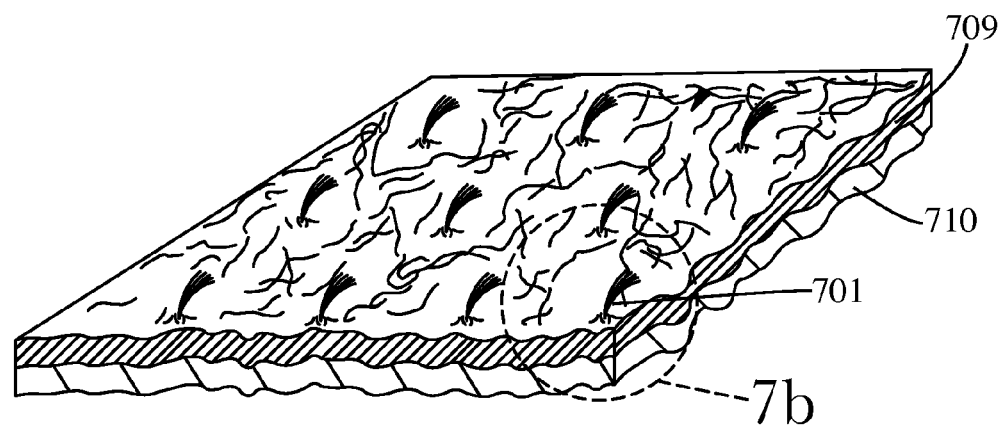
Figure 7A:
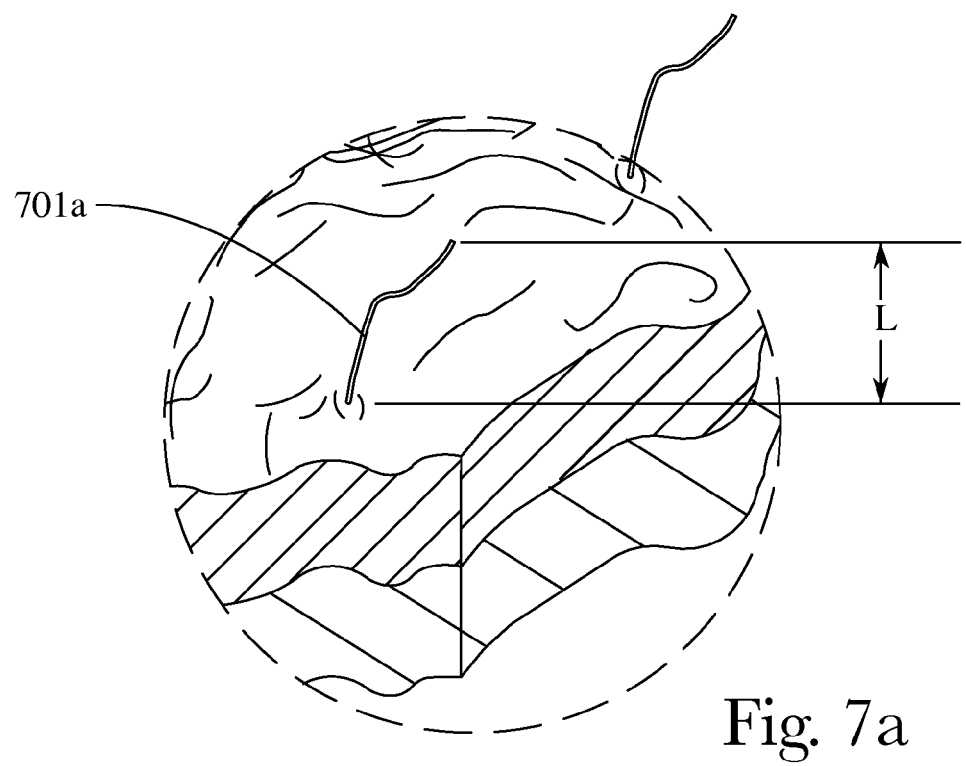
Figure 7B:
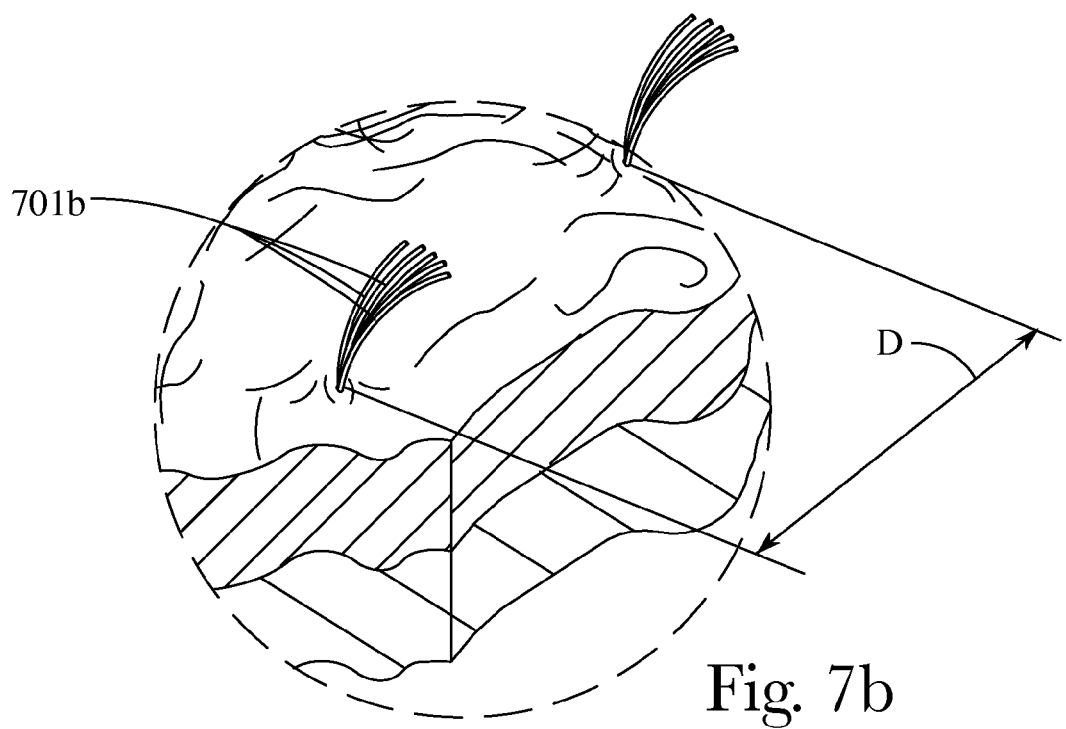
Figure 7C:
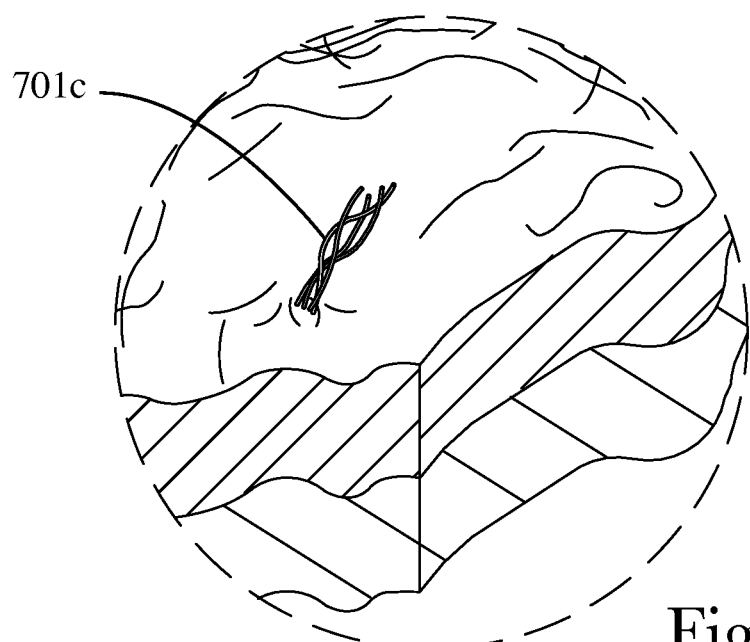
Figure 7D:
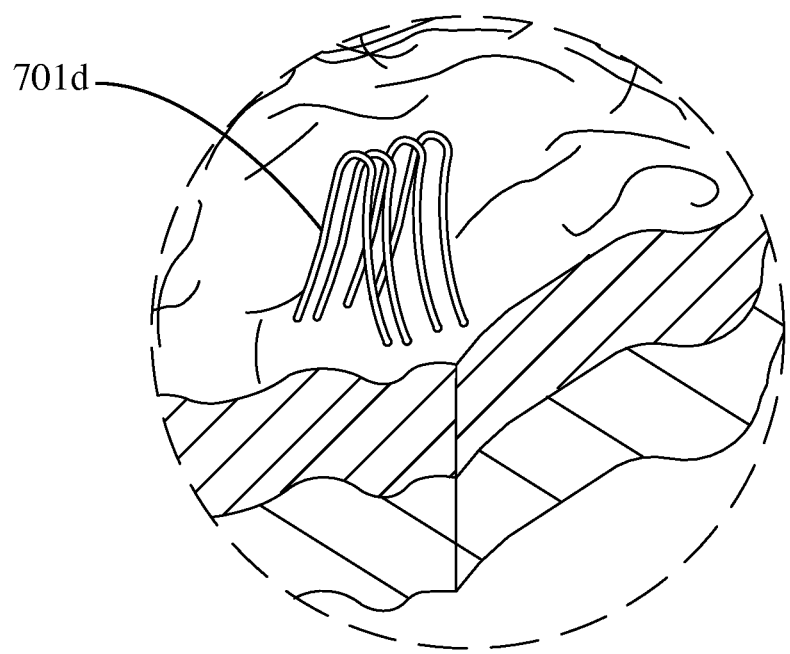

For the purpose of illustration in FIG. 5a the substrate 505 is a rectangular sheet of material designed to be in fluid communication at one end 505a within fluid reservoir 506 as shown in FIG. 5. FIG. 5a shows one end of the substrate end 505a that resides within the fluid reservoir 506. The opposite end of 505b comprises an array of filaments 501. Referring to FIG. 5, when fluid is placed in the reservoir 506 the fluid moves along the fluid transport layer of substrate 505. A top sheet drapes over the fluid transport layer to minimize fluid evaporation and discharge of the fluid's electrical charge as it travels to the filament. Upon reaching the filaments 501, the fluid is taken up the filaments via the capillary action of the compatible materials forming the filaments wherein the fluid ultimately reaches the filament's apex. FIG. 7 illustrates how the filaments 701 protrude through top sheet 709 in such a manner wherein the top sheet 709 does not inhibit the fluid's transport by capillary action through transport layer 710 or along the filaments 701. This embodiment is regarded by one skilled in the art as a multi-layered film.

The top sheet for the substrate above can be virtually any web material, the only requirement being that it have sufficient integrity to be formed into the laminate by the process described below, and that it have sufficiently less elongation properties relative to the transport layer of the substrate such that upon experiencing the strain of fibers from the transport layer of the substrate being urged out-of-plane in the direction of the top sheet so as to rupture the top sheet by tearing due to extensional failure, such that portions of the transport layer can extend through the top sheet and form filaments on first side of the top sheet. In one embodiment top sheet is a polymer film. The top sheet can also be a woven textile web, a nonwoven web, a polymer film, an apertured polymer film, a paper web, (e.g., tissue paper), a foam (e.g., urethane foam sheeting), or the like. Filaments are, in a sense, "punched through" the top sheet and can be "locked" in place by frictional engagement or other means of engagement such as use of an adhesive with these openings, however, the transport of the chargeable fluid along the filaments cannot be hindered by such frictional engagement. Methods for manufacturing top sheets are well known in the art and are disclosed in U.S. Pat. No. 7,410,683.

Alternatively, a transport layer can be treated in such a manner to create a single layer having a bias on one side to transport the fluid while the opposite side is treated to wherein it will maintain the character of fluid moving along the opposite untreated side. This would eliminate the top sheet discussed above. Such treatments include those that will make the substrate resist fluid evaporation loss as well as insulating or resistivity to charge loss by the fluid. Surface treatments to be applied to a substrate may include material such as wax to eliminate the barrier top sheet.

As used in the present invention, the term “filament” means an elongated fiber/fibril or group of fibers/fibrils that are capable of transporting fluids by capillary action. Both the previously mentioned substrate as well as the filaments can comprise the same material or materials being significantly different in terms of their physical and, or chemical characteristics. For example FIG. 7 illustrates the case where the filaments 701 are integrally formed from the substrate’s transport layer 710. Therefore, the integrally formed filaments and substrate transport layer are of the same material.

Where the fluid is aqueous based, the filament and substrate transport layer material are selected from a group of water-based fluid attracting, wettable materials that are hydrophilic. These materials include those selected from the group consisting of cellulosic matter, cellulosic derived polymers including regenerated cellulose, paper, cotton, rayon and combinations thereof. Where the fluids are oil-based, the material is selected from a group of oil wettable, water-repelling, hydrophobic/lipophilic materials. These materials generally comprise synthetic fibers well known in the art. Such synthetic fibers include those disclosed in U.S. Pat. No. 7,410, 983, issued Aug. 12, 2008 and U.S. Patent Application 2009/0289343, published Dec. 21, 2009.

Synthetic fibers are generally made from polymers. These polymers are well known in the art for making the filaments and include homopolymers and copolymer made from a plurality of differing monomers. The filaments may also be made from a single polymer species or from blends of polymers. The filaments may further include any common additives which are safe and effective for their intended purpose and for the intended purpose of the fibrous web, including but not limited to surfactants. Specific polymers comprising the filaments include, but are not limited to those selected from the group consisting of polyolefins, including polypropylene (PP), polyethylene (PE), and poly 4-methylpentene (PMP); polyamides including Nylon®, cellulosic derived polymers including regenerated cellulose, paper, cotton rayon; polyesters including polyethylene terephthalate and combinations and/or blends of all the afore mentioned polymers.

In any case, the fluid emitter filaments and substrate transport layer must be compatible with the fluid to be used. A guideline relative to selecting a suitable material is to select materials by matching the surface energy of the material to the surface tension of the fluid. Those skilled in the art will recognize that surface contact angle provides a convenient method of determining the match between the surface tension of the fluid and the surface energy of the materials. Fluid material suitability is indicated when the static contact angle is less than 30 degrees preferably less than 20 degrees more preferably less than 15 degrees. The static contact angle can be conveniently determined using a Kruss DSA 100 system available from Kruss USA, Nazareth, Pa., USA.

FIG. 7 illustrates the filament array. FIG. 7*a* through FIG. 7*d* illustrates the fact that filaments can consist of a single strand or fiber 701*a* in FIG. 7*a*, a group or bundle of independent fibers 701*b* in FIG. 7*b*, a group of organized fibers 701*c* in FIG. 7*c* and looped singular and, or multiple of fibers 701*d* in FIG. 7*d*. Filaments normally comprises from 1 to about 50, alternatively from about 3 to about 30 and alternatively from about 5 to about 20 distinct strands or fibers.

FIG. 7*b* illustrates that the filaments 701*b* are evenly spaced a distance “D” from each other in order to prevent problems such as electrical arching and, or electrical field neutralization among the filaments. This distance D has values from about 1.0 mm to about 100 0 mm, alternately from about 1.0 mm to about 35.0 mm, alternately from about 3.0 mm to about 15.0 mm and finally alternately from about 4.0 mm to about 5.0 mm FIG. 7*a* illustrates that the filaments 701*a* have lengths “L” that is measured from the planar surface or face of the substrate 705 to the filament apex 701*a*. L is typically from about 0.50 mm to about 10.00 mm, but ultimately the length L depends on the fluid selected and the degree of the electrical field intensity.

Filament lengths (L) are required to be from about 1 to about 10 mm, alternatively from about 1 to about 5 mm and alternatively from about 2 to about 4 mm to produce the sufficient electrical field intensity. It is important that when there is an array of filaments, that each filament’s apex is approximately the same length (L). One way to insure this is upon forming and attaching the filaments having loose ends, the loose ends are cropped to a uniform filament length.

The filaments move the electrically chargeable fluid along the filament a distance (L) by means of capillary action to arrive at the apex wherein when charged, the fluid is exposed to an electric field to produce an electro statically charged fluid particle droplets having a particle droplet size from about 1.0 nm to about 5000 nm, alternatively from about 5.00 nm to about 500.00 nm and also alternatively from about 10.00 nm to about 100.00 nm. The transport layer must exhibit a sufficient amount of capillary action in order to saturate the fluid emitter filament(s) so that sufficient fluid is available for electrostatic spraying. Likewise, sufficient capillary action is required to draw fluid from the fluid source to the apex of the filament to maintain the electrostatic spraying. Once the capillary forces are satisfied, electrical power is applied to achieve supplemental fluid transport due to the attractive forces by the electrical field to attract fluid towards the grounding surface. This supplemental fluid attraction to the grounding surface is difficult to differentiate from the capillary action.

The number of filaments per unit area of substrate, i.e., the area density of the filaments, can vary from 1 filament per unit area or square centimeter ($cm^2$) to as high as 10 filaments per $cm^2$. There can be at least 1, or at least 10 filaments per $cm^2$, depending on the end use. In general, the area density need not be uniform across the entire area of substrate, but filaments can be only in certain regions of the substrate, such as in regions having predetermined shapes, such as lines, stripes, bands, circles, and the like.

A variety of methods known in the art may be utilized for forming filaments. In that regard the requirement that the filaments transport the chargeable fluid ultimately dictates the material chosen as the filament. Where the filaments are integrally formed from the substrate's transport layer, an effective means of producing filaments is by needle punching the substrate. Needle punching involves pushing needles into and through the substrate to urge individual fibers or groups of fibers making up the transport layer out-of-plane in the Z-direction or horizontal plane of the substrate at discrete, localized, portions of substrate to create the filaments. The urging out of the Z-plane can be due to fiber displacement, i.e., the fiber is able to move relative to other fibers and be "pulled," so to speak, out-of-plane. More often, however, for most woven and nonwoven substrates, the urging out-of-plane is due to the fibers of filaments having been at least partially plastically stretched and permanently deformed or broken to form filaments. By urging the fibers out of their usual plane the deformed fibers may take the form of free-ended fibers, looped fibers, molded protrusions of fluid transport material, embroidered tuffs and apertured polymer films. Depending on the desired height of filament, the constituent fibers of nonwoven substrate can exhibit an elongation to break fibers 9 to form the filaments. These filaments can be plastically deformed and extended fibers of the substrate and are, therefore, integral with the substrate. As used herein, "integral" is to be distinguished from fibers introduced to or added to a separate substrate for the purpose of making filaments, as is commonly done in conventional carpet making, for example.

Whether loose ended or looped, the filaments are substantially aligned such that they have a distinct linear orientation and a longitudinal axis. The filament also has a transverse axis generally orthogonal to longitudinal axis. Elongation to break can be determined by simple tensile testing, such as by use of Instron° tensile testing equipment, It can be appreciated that a suitable woven and nonwoven substrate should comprise fibers capable of experiencing sufficient plastic deformation and tensile elongation, or are capable of sufficient fiber mobility, such that either loose end or looped fibers are formed. However, it is recognized that a certain percentage of fibers urged out of the plane of the first surface of substrate will not form a loop, but instead will break and form loose ends. Loose fiber ends are the result of forming filaments from nonwoven webs consisting of, or containing, cut staple fibers. In such a case, some number of the staple fiber ends may protrude into the filaments, depending upon such things as the number of staple fibers in the web, the staple fiber cut length, and the height of the filaments.

These fibers include round and non-round fibers. The term "non-round fibers" describes fibers having a non-round cross-section, and includes "shaped fibers" and "capillary channel fibers." The physical structure of the filament can take any number of forms but must maintain a structure capable of delivering water-based or oil-based fluids. The filaments can be solid or hollow, and they can be tri-lobal, delta-shaped, and are preferably fibers having capillary channels on their outer surfaces. The capillary channels can be of various cross-sectional shapes such as U-shaped, H-shaped, C-shaped and V-shaped.

D. The Counter Electrode

The substrate and, or filaments are selected such that they transport fluid by capillary action to the apex. Once the fluid arrives at the apex and is charged there is a point along the filament, close to or even at the apex of the filament when the charged fluid reaches its highest electrical potential relative to an area of lowest electrical potential of the system. In the system disclosed herein, the point of lowest electrical potential is a counter electrode. When at it's point of highest electrical potential, the presence of the counter electrode establishes an electrical field intensity sufficient to cause the fluid to form a stream of very small droplets by a process commonly referred to as electro-hydrodynamic spraying or commonly known in the art as "E-spraying." FIG. 1 illustrates this phenomenon wherein the electrically charged fluid at the apex of the filament 101a forms a stream of charged droplets 102 in the presence of counter electrode 108 to create the desired fluid droplets The counter electrode also known by those skilled in the art as the "ground" and may take the form of any number of, animate or inanimate objects. For means of illustration FIG. 9 of apparatus Example 2, the person's eyeball is the target or the counter electrode in the system. FIG. 10 similarly illustrates this point wherein rather that the eyeball, apparatus Example 3's moist tissues within the throat act as the counter electrode and are the target for the charged droplets to be delivered.

The electrical field intensity is increased in one of two ways: the distance between the apex of the filaments and the counter electrode are fixed and the potential or voltage increased or alternatively the voltage is fixed and the distance between the apex of the filament and the counter electrode is reduced. Regardless of the approach, the filaments protrude from the substrate and are sufficiently distant from the counter electrode to create the appropriate electrical field intensity sufficient to cause the fluid to form an "e-spray." Those skilled in the art will recognize that the field required to induce an e-spray varies depending upon the properties of the fluid as previously discussed. The minimum electrical field intensity required to initiate the spray of very small droplets is generated when the filaments are of length L greater than about 0.5 mm.

The very small fluid droplets coming from the filaments depend on several factors including the hydrophobicity of the fluid as measured by its surface tension and the geometry of the filaments. The field intensity at the filament apex required to initiate a spray of very small droplets generally increases as the hydrophobicity of the fluid increase. The field intensity required to initiate the spray is generally reduced as the diameter of the filament tip (including fluid) is reduced. Generally the threshold field strength defined herein as the voltage of the charged fluid at the apex of the filament, divided by the shortest linear distance from the filament's apex to the low potential surface or ground (at about a zero angle of the apex to the ground) is about $5 \times 10^4$ V/m. The upper limit of the field strength is established by the breakdown voltage of air. This voltage is generally understood by those skilled in the art as the voltage necessary to ionize the air molecules that results in a spark as is what transpires in the case of atmospheric lightning. Although this phenomenon depends to some degree on factors including, but not limited to the shape of the electrode surfaces and humidity of air, the breakdown of air is generally about $3 \times 10^6$ V/m.

In an alternative embodiment the high voltage electrode that charges the fluid forms one layer of the emitter substrate. A second layer on the side opposite that of the high voltage electrode forms the counter electrode or the lowest electrical potential separated by an insulating element to prevent discharge from the high and low voltage electrodes. Such insulation can be the substrate itself or a layer affixed to the substrate. In another embodiment the high voltage electrode is directly behind or at the rear of the substrate at the filament array. In this embodiment, the area of lowest electrical potential is a surface just above the filament apex. The substrate has gaps sufficient to avoid the charged fluid from discharging or grounding into the substrate.

In another embodiment, additional electrodes are added to act as accelerating electrodes. In this embodiment the fluid charging electrode can be positioned in the fluid or directly behind the filaments as described above. There is a low potential electrode or counter ion in the form of a grounding plate opposite the filaments. There is a third electrode positioned between the filament and the low potential electrode at a voltage between that of the high voltage filament apex and the counter electrode. This electrode may be positioned at any position between the apex and the counter electrode, but is most advantageous when closer to the high potential filament. The distances or height between the filament apex and the accelerating electrode is from about 1 mm to about 20 mm and alternatively from about 2 mm to about 10 mm. The potential of the accelerating electrode should be selected so as to obtain and e-spray but be below the breakdown voltage of air ($3 \times 10^6$ V/m).

In another embodiment the high voltage electrode forms one layer of the emitter element and a second emitter element forms a lower potential electrode with the two elements separated by an insulating element sufficient to prevent discharge between the two electrodes.

EXAMPLES

Emitter Substrate Example 1

An emitter is prepared by forming a multilayer sheet comprising an aluminum foil base layer, a second layer comprising a 100 gm/m$^2$ paper and a third layer comprising one millimeter polyethylene film. The composite structure thus formed is needle punched using commercial felting needles from Groz-Beckert (needle specification being a number 15×17×25×38×63 needle for forming the filaments). The filaments protrude about 2 mm above the polyethylene face or top sheet of this composite structure.

Emitter Substrate Example 2

An emitter is prepared by forming a multilayer sheet comprising a copper foil base layer, a second layer comprising 600 threads per square inch woven cotton fabric and a third layer comprising two millimeter polyethylene film. The composite structure thus formed is needle punched using commercial grade felting needles from Groz-Beckert (needle specification being a number 15×17×25×38×9 needle) for forming the filaments) The filament protrude about 2 mm above the polyethylene face or top sheet of the composite structure Emitter Substrate Example 3

An emitter is prepared by forming a multilayer sheet comprising a nickel foil base layer, a second layer comprising 100 grams/meter$^2$ polyethylene staple fiber non-woven comprised of 10 denier fibers about 1-5 mm and a third layer comprising 2 millimeter polyethylene film. The composite structure thus formed is needle punched using commercial grade felting needles from Groz-Beckert (needle specification being a number 15×17×25×38×9 needle) to form filament elements protruding about 2 mm above the polyethylene face or top sheet of the composite structure Emitter Substrate Example 4

Figure 8:
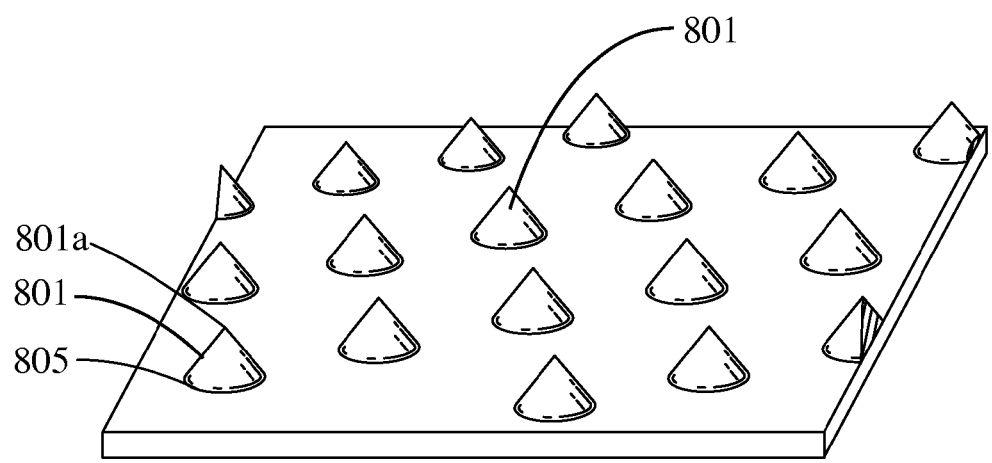

A polyethylene film as described in U.S. Pat. No. 3,929,135 is made by hydro formation creating an array of 0.20 mm cone-shaped apertures with tapered capillaries separate from their centers by about 5.0 mm as illustrated in FIG. 8

After pumping a slurry comprising about 2 to about 5% cellulosic fibers and water onto an indented side of a screen, a pump pulls a vacuum from the opposite side of the screen of the paper slurry sufficient to dewater the pulp to less than about 25% residual water. A drier, usually an oven dries this composite pulp-based structure.

Apparatus Example 1

An Air Purifying Device

Figure 3:
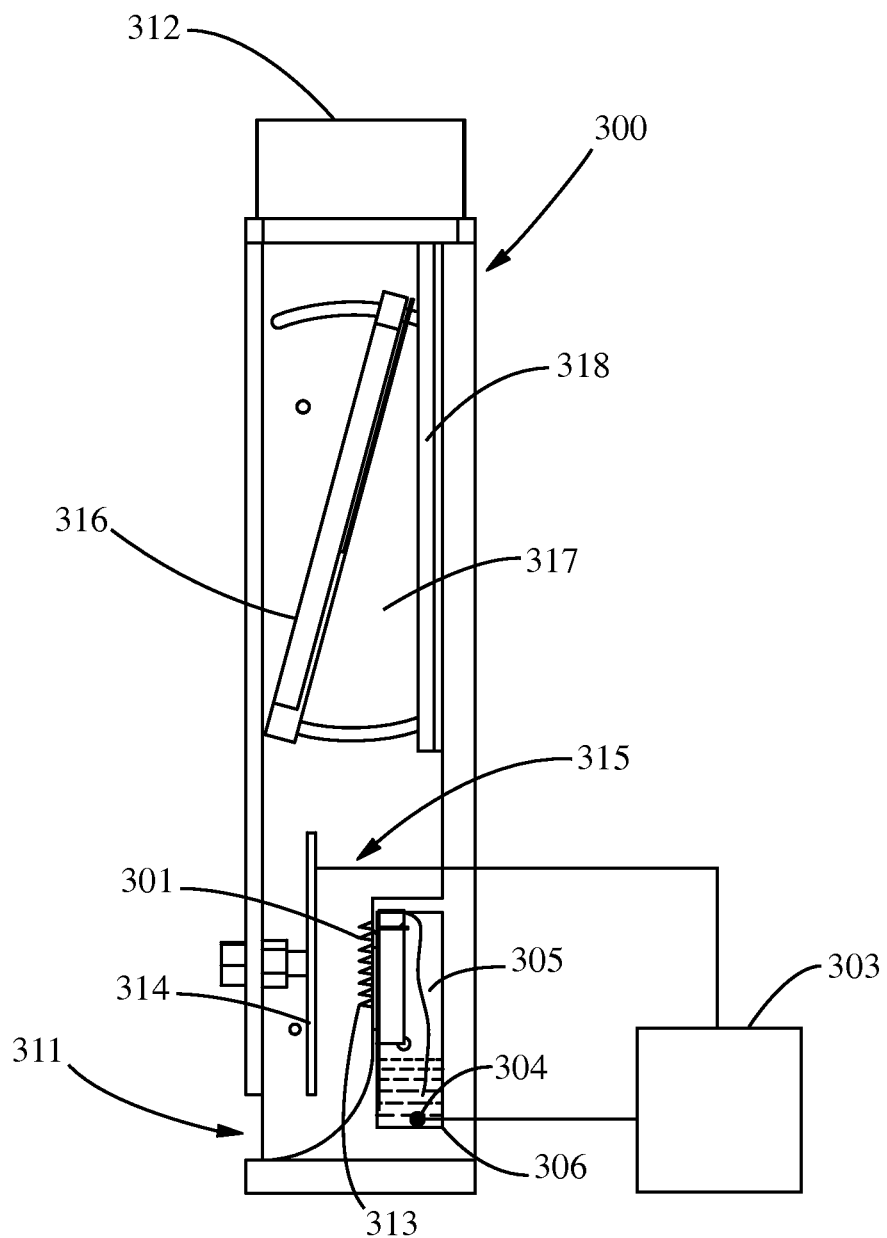
Figure 4:
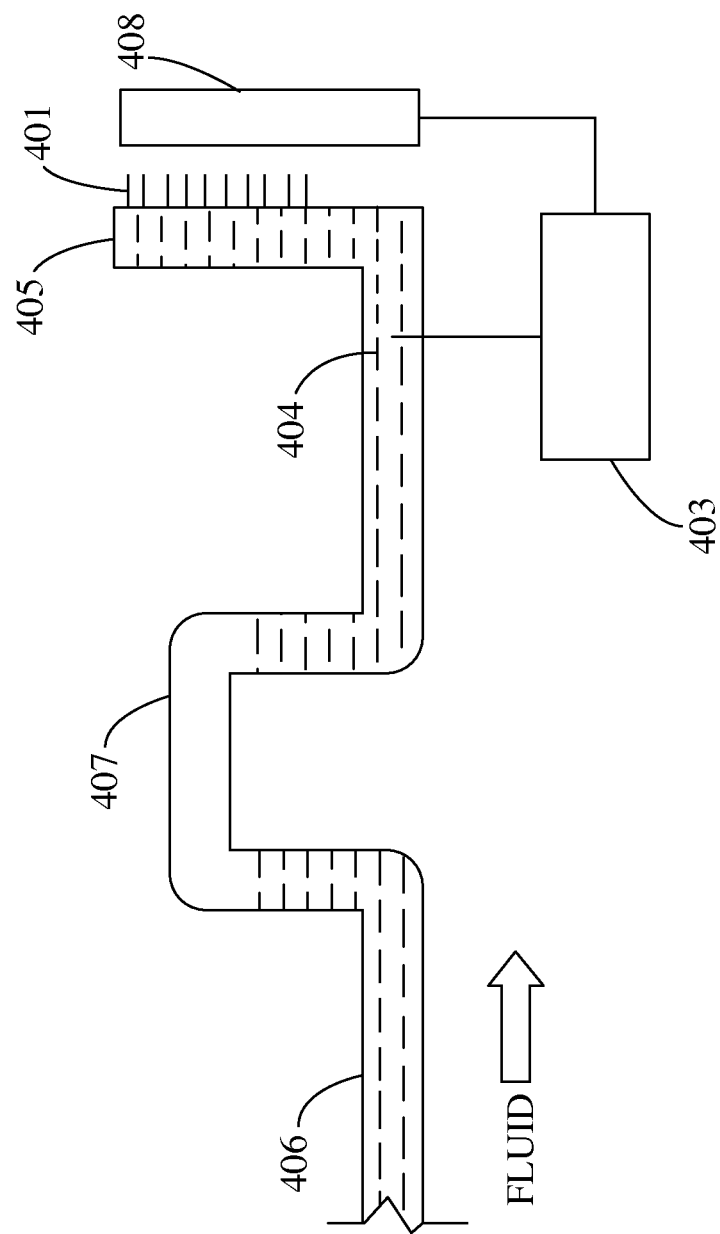

FIG. 3 illustrates a device utilizing the apparatus of the present invention and employing Emitter Substrate Example 1 as the substrate 305. Accordingly, the air purifying apparatus 300 comprises an inlet 311 into which a flow of input air is directed, said input air containing a plurality of particulates; an outlet 312 out of which a flow of output air is directed; at least one fluid emitter 313 through which a fluid is converted into a plurality of electrically charged droplets when the fluid in reservoir 306 is charged when electrode 304 is energized by supply 303. In the presence of the requisite electrical field intensity created between the emitter 313 and the grounding plate 314 chargeable fluid droplets are formed and intermix with said input air. The droplets attract the plurality of particulates in the supply air, thereby forming a plurality of charged complexes in a first zone 315; wherein said complexes are removed from said input air 311 wherein a deflecting element 316 comprising a third polarity and disposed in a second zone 317, said second zone 317 in air flow communication with and downstream from said first zone 311; and a collective surface 318 comprising a fourth polarity and disposed in said second zone 317, wherein said deflecting element 316 deflects a final portion of said plurality of charged complexes onto said collective surface 318 resulting in reduced particulates in said output air.

Apparatus Example 2

An Eye Treatment Device

The present apparatus illustrated in FIG. 9 employs the Emitter Substrate Example 1. Adhering to substrate 905 is an aluminum foil backing sheet 904 acting as the electrical charging electrode to provide 4 kV of high voltage power to the foil backing sheet by using high voltage power source 903. The user 920 places their eye 921 within the proximity of the device so as to establish the grounding necessary to create the required electrical field intensity to produce the spray of small charged droplets of an isotonic fluid from the reservoir 906. These droplets are drawn to the surface of the eye 921 to provide treatment to the eye for desired benefits including arresting a condition commonly referred to as “tired eyes.”

Apparatus Example 3

Oral Treatment Device

The present apparatus illustrated in FIG. 10 employs the Emitter Substrate Example 2.

Adhering to substrate 1005 is a copper foil base layer 1004 to minimize depletion of the fluid’s electrical charge. The electrical charging electrode is located within the fluid reservoir 1006 and providing 4 kV of high voltage power to the fluid using high voltage power source 1003. The third layer 1009 insulates the fluid from loss of electrical charge and evaporation. The user 1020 places their open mouth 1021 within the proximity of the device so as to establish the grounding necessary to create the required electrical field intensity to produce the spray of small charged fluid droplets of an isotonic fluid from reservoir 1006. Those droplets are drawn to the surface of the tissues inside the mouth 1021 and throat 1022 to provide treatment to the inside of the mouth and throat for desired benefits including administering orally absorbable medicaments including local pain medicine commercially found in sore throat products.

Apparatus Example 4

Hard Surface Cleaning Device

The present apparatus illustrated in FIG. 11 employs the Emitter Substrate Example 3. Behind substrate 1105 is copper plate 1104 and a second electrode within fluid reservoir 1106 remaining in fluid communication with the fluid therein. Together these electrodes providing about 4 kV of high voltage power to the fluid using high voltage power source 1103. A plurality of arms 1123 are directly to the contact surface 1120. These arms 1123 are of equal length and terminate with rollers 1124 at their proximal ends. Proximity switches located in or about the rollers 1124 open the circuit upon rolling the device to allow power to flow from supply 1103 to copper plate 1104. The arms 1123 are designed to be of such a length to establish the electrical field intensity sufficient to generate charged fluid droplets of fluids containing hard surface cleaning and, or polish formulations to deposit onto surface 1120.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or patent application is hereby incorporated herein by reference in their entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for production of very small electrically charged fluid droplets comprising:
   a. an electrically chargeable fluid;
   b. an electrical fluid charger in fluid communication with the chargeable fluid;
   c. a fluid emitter in fluid communication with the chargeable fluid comprising a substrate having evenly spaced filaments of approximately equal length affixed thereto; and
   d. a counter electrode;
   where upon the electrically chargeable fluid reaches an apex of the filament and is electrically charged, the distance between the filament apex and the counter electrode is sufficient to create an electrical field intensity wherein the electrically charged fluid is converted into a stream of very fine and charged fluid droplets moving from the filament's apex in the direction of the counter electrode along the electrostatic field's force lines formed between the filament's apex and the counter electrode, wherein the electrically chargeable fluid has a viscosity of less than 1000 centistokes, and is selected from the group consisting of water-based fluid and oil-based fluids whose selection is based upon the fluid's compatibility relative to the material comprising the fluid emitter so to create a fluid flux between the fluid moving from the layer of the substrate and the apex of the filament of a sufficient level to form a sustainable stream of very fine and charged fluid droplets at the filament's apex as the fluid is electrically drawn towards the counter electrode.

2. The apparatus of claim 1 wherein the electrically chargeable fluid is oil-based and selected from fluids that are is immiscible in water and do not dissolve in water.

3. The apparatus of claim 2 wherein the electrical fluid charger comprises a high voltage electrode comprising material compatible with the chargeable fluid, selected from the group consisting of metals, carbon, conductive plastics, carbon containing conductive plastics and combinations thereof.

4. The apparatus of claim 2 wherein the electrically chargeable fluid is a non-aqueous composition comprising low basis weight polymer films to provide hair styling adhesive polymers.

5. The apparatus of claim 1 wherein the electrically chargeable fluid is water-based and selected from fluids that are miscible in water and dissolve in water.

6. The apparatus of claim 5 wherein the electrically chargeable fluid is water.

7. The apparatus of claim 6 wherein the electrically chargeable fluid further comprises solutions, dispersions and emulsions of materials selected from the group consisting of salts especially isotonic salt solutions, bioactive materials including antimicrobials, bleaches, catalysts, amine and aldehyde reactive species, perfuming raw materials, formulated perfumes, surfactants, waxes, oils, polymers, bioavailable, over-the-counter and prescriptive, ingredients including antitussives, decongestants, analgesics, vitamins, and other topical medicinal compounds and agents, coloring materials, color cosmetics, keratinous tissue cleansing, sanitizing, exfoliating, conditioning, styling, toning and moisturizing agents and combinations thereof.

8. The apparatus of claim 7 wherein the materials are bioactive materials selected from the group consisting of antimicrobials, bleaches, catalysts, amine and aldehyde reactive species and combinations thereof.

9. The apparatus of claim 8 wherein the bioactive materials are selected from the group consisting of keratinous tissue cleansing, sanitizing, exfoliating, conditioning, styling, toning and moisturizing agents and combinations thereof.

10. The apparatus of claim 1 wherein the electrically chargeable fluid has a resistivity from about 1 kΩ/cm to about 1000 MΩ/cm.

11. The apparatus of claim 10 wherein the electrically chargeable fluid has a resistivity from about 100 kΩ/cm to about 500 MΩ/cm.

12. The apparatus of claim 1 wherein the filaments are formed from the material comprising the substrate displaced in a direction perpendicular to the substrate's X-Y-plane.

13. The apparatus of claim 1 wherein the filaments are selected from the group consisting of free-ended fibers, looped fibers, molded protrusions of fluid transport material, embroidered tuffs, apertured polymer films, sewn tuffs and combinations thereof.

14. The apparatus of claim 13 wherein the filaments of the fluid emitter comprise an average of about 1 to about 50 distinct fibers.

15. The apparatus of claim 14 wherein the filaments of the fluid emitter comprise an average of about 5 to about 20 distinct fibers.

16. The apparatus of claim 1 wherein the array of filaments is of a length (L) to form charged fluid droplets in the presence of the counter electrode, the droplets having an average diameter from about 1.0 nm to about 5000 nm.

17. The apparatus of claim 16 fluid wherein the array of filaments is of a length (L) to form charged fluid droplets in the presence of the counter electrode, the droplets having an average droplet diameter from about 5.0 nm to about 500 nm.

18. The apparatus of claim 17 wherein the array of filaments is of a length (L) to form charged fluid droplets in the presence of the counter electrode, the droplets having an average droplet diameter from about 10.0 nm to about 50.0 nm.

19. The apparatus of claim 18 wherein the fluid emitter has a distance (D) between filaments at the surface of the substrate equal to the average length (L).

20. The apparatus of claim 18 wherein the fluid emitter has a distance (D) at the surface of the substrate one and a half times the average length (L).

21. The fluid emitter of claim 18 wherein the distance (D) at the surface of the substrate is twice the average length (L).

22. The apparatus of claim 1 wherein the substrate additionally comprises a top sheet having a filament array protruding through the top sheet in the direction of the counter electrode.

23. The apparatus of claim 1 wherein the electrically chargeable fluid is held within a fluid reservoir in fluid communication with the electrical fluid charger.

24. The apparatus of claim 1 wherein the electrical fluid charger is in proximity sufficient to charge fluid saturating the emitter substrate.

25. The apparatus of claim 24 wherein the proximity is direct contact of the adjacent surfaces of the charging electrode and the emitter substrate.

26. The apparatus of claim 24 wherein the electrical fluid charger has an electric field strength voltage gradient capable of transferring the electrical charge to the electrically chargeable fluid to produce electrical field strength in the range from about 500 volts per centimeter (V/cm) to about 5000 V/cm.

27. The apparatus of claim 26 wherein the electric fluid charger comprises a plurality of electrodes one being at a point in the fluid reservoir to remain in fluid communication with the fluid in the reservoir.

28. The apparatus of claim 24 wherein the electrical fluid charger has an electric field strength voltage gradient capable of transferring the electrical charge to the electrically chargeable fluid to produce electrical field strength in the range from about 1000 V/cm to about 3000 V/cm.

29. The apparatus of claim 1 wherein the counter electrode is selected from the group of animate objects, inanimate objects and combinations thereof.

30. The apparatus of claim 29 wherein the inanimate objects are selected from the group consisting of household surfaces, fabrics, car interiors, convertible tops and combinations thereof.

31. The apparatus of claim 29 wherein the animate objects are selected from the group consisting of skin, hair, moist tissue, finger nails and combinations thereof

* * * * *